(12) United States Patent
Bhaskaran et al.

(10) Patent No.: US 8,513,203 B2
(45) Date of Patent: Aug. 20, 2013

(54) COMPOSITION AND METHOD THEREOF

(75) Inventors: Sunil Bhaskaran, Maharashtra (IN); Mohan Vishwaraman, Maharashtra (IN)

(73) Assignee: Indus Biotech Private Limited, Maharashtra (IN)

( * ) Notice: Subject to any disclaimer, the term of this patent is extended or adjusted under 35 U.S.C. 154(b) by 51 days.

(21) Appl. No.: 13/160,347

(22) Filed: Jun. 14, 2011

(65) Prior Publication Data

US 2012/0282332 A1    Nov. 8, 2012

(30) Foreign Application Priority Data

May 2, 2011    (IN) .......................... 1367/MUM/2011

(51) Int. Cl.
    *A01N 45/00*    (2006.01)
(52) U.S. Cl.
    USPC ........................................... 514/26; 424/452
(58) Field of Classification Search
    USPC .......................................... 424/452; 514/26
    See application file for complete search history.

(56) References Cited

U.S. PATENT DOCUMENTS

| | | | |
|---|---|---|---|
| 5,607,965 A * | 3/1997 | Kondo et al. | ................. 514/456 |
| 5,707,631 A | 1/1998 | Lieberman | |
| 6,080,401 A | 6/2000 | Reddy et al. | |

OTHER PUBLICATIONS

Moosa et al., Hypolipidemic effects of fenugreek seed powder, 2006, Bangladesh Journal of Pharmacology, pp. 64-67.*
Yoshikawa et al., Medicinal foodstuffs. IV. Fenugreek seed. (1) structures of trigoneosides Ia, Ib, IIa, IIb, IIIa, and IIIb, new furostanol saponins from the seds of Indian *Trigonella foenum-graecum* L., 1997, Chemical and Pharamceutical Bulletin, vol. 45 issue 1, pp. 81-87.*
Rayyan et al., Flavone C-Gylcosides from Seeds of Fenugreek, *Trigonella foenum graecum* L., 2010, Journal of Agricultural and Food Chemistry, vol. 58 No. 12, pp. 7211-7217.*

Chen, Y.-M. et al. 2004 "Pentoxifylline suppresses renal tumour necrosis factor-α and ameliorates experimental crescentic glomerulonephritis in rats" *Nephrol Dial Transplant* 19: 1106-1115.
Kumar, A. et al. 2002 "Validation of an Indian version of the Health Assessment Questionnaire in patients with rheumatoid arthritis" *Rheumatology* 41:1457-1459.
Ahamadiani, A. et al. 2001 "Anti-inflammatory and antipyretic effects of *Trigonella foenum-graecum* leaves extract in the rat" *Journal of Ethnopharmacology* 75: 283-286.
Chopra, A. et al. 2010 "Ayurveda-modern medicine interface: A critical appraisal of studies of Ayurvedic medicines to treat osteoarthritis and rheumatoid arthritis" *Journal of Ayureveda & Integrative Medicine* 1: 190-198.
Khan, M.O.A. et al. 2011 "Clinical evaluation of herbal medicines for the treatment of rheumatoid arthritis" *Pakistan Journal of Medicine* 10: 51-53.
Murakami, T. et al. 2000 "Medical foodstuffs. XVII. Fenugreek seed. (3): Structures of new furostanol-type steroid saponins, Trigoneosides Xa, Xb, XIb, XIIa, XIIb, and XIIIa, from the seeds of Egyptian *Trigonella foenum-graecum* L." *Chem Pharm Bull* 48: 994-1000.
Sato, S. and Koide, T. 2010 "Synthesis of vicenin-1 and 3, 6,8- and 8,6-di-C-β-D-(glucopyranosyl-xylopyranosyl)-40,5,7-trihydroxyflavones using two direct C-glycosylations of naringenin and phloroacetophenone with unprotected D-glucose and D-xylose in aqueous solution as the key reactions" *Carbohydrate Research* 345: 1825-1830.
Vyas, S. et al. 2008 "Analgesic and Anti-Inflammatory Activities of *Trigonella foenum-graecum* (Seed) Extract" *Acta Poloniae Pharmaceutica- Drug Research* 65: 473-476.
Wagner, H. et al. 1973 "Vicenin-1 and -2 in the seeds of *Trigonella* and *Foenumgraecum*" *Phytochemistry* 12: 2548.
Yoshikawa, M. et al. 1997 "Medical foodstuffs. IV. Fenugreek seed. (1): Structures of Trigoneosides Ia, Ib, IIa, IIb, IIIa and IIIb, new furostanol saponins from the seeds of Indian *Trigonella foenum-graecum* L." *Chem Pharm Bull* 45: 81-87.

* cited by examiner

*Primary Examiner* — Ali Soroush
(74) *Attorney, Agent, or Firm* — Knobbe, Martens, Olson & Bear, LLP

(57) ABSTRACT

The present disclosure relates to a composition comprising Trigoneoside Ib and Vicenin-1 for treatment and management of Goodpasture's disease, Glomerulonephritis, Rheumatoid Arthritis, Systemic Lupus Erythematosus and Idiopathic Thrombocytopenia Purpura. The present disclosure also relates to a method of obtaining the said composition from *Trigonella foenum-graecum*.

22 Claims, 3 Drawing Sheets

COMPOSITION AND METHOD THEREOF

CROSS-REFERENCE TO RELATED APPLICATIONS

This application claims the benefit of Indian Patent Application No. 1367/MUM/2011 filed May 2, 2011, which is hereby expressly incorporated by reference in its entirety.

BACKGROUND OF THE INVENTION

1. Field of the Invention

The present disclosure relates to a composition comprising Trigoneoside Ib and Vicenin-1 and the method of obtaining the said composition. The present disclosure further relates to the application of the composition for treatment and management of autoimmune disorders such as Goodpasture's disease, Glomerulonephritis, Rheumatoid Arthritis, Systemic Lupus Erythematosus and Idiopathic Thrombocytopenia Purpura.

2. Description of the Related Art

Autoimmune disorders such as Goodpasture's disease, Glomerulonephritis, Rheumatoid Arthritis, Systemic Lupus Erythematosus and Idiopathic Thrombocytopenia Purpura demonstrate excessive production of auto-antibodies that cause severe damage to cells, tissues, organs etc. These diseases are characterized by loss of body's tolerance towards self-antigens and subsequent activation of immune responses leading to damage. Hereditary predispositions and environmental factors are predominant causes of these diseases.

Goodpasture's disease and glomerulonephritis are characterized by deposition of antibodies along the glomerular basement membrane (GBM) in the kidneys resulting in extracapillary glomerulonephritis. These diseases are commonly termed as anti-glomerular basement membrane (anti-GBM) diseases. Patients suffering from anti-GBM diseases have only 10% chance of renal survival. Goodpasture's disease is a rare disease occurring in one in million people. Auto-antibodies mediated kidney damage is the primary concern in Goodpasture's disease. Some patients also develop pulmonary hemorrhage however the damage caused to lungs by anti-GBM antibodies is not permanent and rarely fatal when compared to damage to the kidneys.

Existing treatment for Goodpasture's disease or glomerulonephritis includes plasmapheresis or plasma exchange procedure which eliminates circulating anti-GBM antibodies from the blood. Risk of exposure to blood products, hematoma, transfusion reaction, and transfusion transmitted diseases are major complications which are associated with plasmapheresis. Other treatment options include administration of immunosuppressive agents like corticosteroids and cyclophosphamide which are prescribed to manage progressive kidney failure and bleeding in the lungs. These drugs suppress immune response in a non-specific way and increase the chances of patients getting opportunistic infections. Current line of treatment for anti-GBM diseases does not completely control the disease. Progression of the disease to end stage organ failure increases the risk of mortality.

Rheumatoid Arthritis (RA) is a chronic, progressive disease affecting about 1% of the world's population which is mediated through auto antibodies. Similar to Goodpasture's disease, RA is characterized by loss of body's tolerance towards self-antigens and subsequent activation of immune responses leading to tissue damage. Production of auto-antibodies targeting the synovial membrane, cartilage, and underlying bone joint defines pathogenesis of RA. Deformation of the joints results in severe disability and reduced quality of living. Common symptoms include joint pain, stiffness and swelling of joints, movement disability, muscle weakness, fever and general feeling of being unwell. Increased levels of C-reactive protein and rheumatoid factor in the blood are diagnostic indicators of RA. Existing treatment for RA include disease modifying anti-rheumatic drugs (DMARDs) like hydroxychloroquine, immunosuppressants like azathiprine, corticosteroids, selective COX-2 inhibitors, NSAIDs, and analgesics for symptomatic relief Chronic use of analgesics, NSAIDs cause ulcers and have low tolerance with most patients and selective COX-2 inhibitors are associated with cardiac toxicity.

Immunosuppressants are the major line of treatment for RA. As discussed earlier, these drugs suppress immune response in a non-specific way and give raise to life threatening complications. Biological drugs like TNF inhibitors namely adalimumab, etanercept, infliximab etc., IL-1 receptor antagonists namely Anakinra and IL-6 receptor antagonists namely tocilizumab are widely used in treating RA. These drugs are designed to affect the biochemical pathways that cause inflammation of joint and joint damage by acting as antagonists of the cytokine receptors. One major disadvantage of biologicals is that on chronic usage patients become refractive to these drugs and the efficacy of treatment declines. Due to the toxicity profile, many of these drugs are recommended only for patients who do not respond to other RA treatments.

Systemic Lupus Erythematosus (SLE) is a multisystem autoimmune disorder which is clinically diagnosed on the basis of features like joint pain, fever, fatigue, skin lesions, photosensitivity, chest pain, hair loss, mouth sores etc., supported by findings of auto-antibodies in the blood and excessive serum protein in the urine. Kidney failure is one of the major complications of SLE. More than 50% of SLE patients develop kidney failure due to deposition of antibodies in the glomeruli and require kidney dialysis or transplantation. Other complications mediated by auto-antibodies include damage to the lungs, heart, hemolytic anemia, thrombocytopenia, cerebral dysfunction etc. Existing treatment options for SLE includes NSAIDs, antimalarial agents, corticosteroids and methotrexate for alleviating musculo-skeletal and cutaneous manifestations. According to the USFDA, current line of treatment for SLE have issues like incompletely controlled disease, progression to end-stage organ failure and debilitating side effects (Guidance for Industry: Systemic Lupus Erythematosus—Developing Medical Products for Treatment, June 2010).

Idiopathic thrombocytopenia purpura (ITP) is a bleeding disorder caused by drastic reduction in platelets. ITP can be triggered by infections, immune disorders like SLE, certain drugs, pregnancy etc. Although the exact mechanism of ITP pathogenesis is still not clear, ITP is largely attributed to destruction of platelets by anti-platelet antibodies since more than 50% of ITP patients test positive for platelet associated antibodies (Gernsheimer, 2009). Existing treatment options for ITP include (i) drugs like corticosteroids and intravenous immunoglobulin which interfere with clearance of antibody-coated platelets; (ii) nonspecific T-cell immunosuppression by drugs like azathioprine, cyclophosphamide, cyclosporine; (iii) mycophenolate mofetil and biologicals like rituximab which interfere with antibody synthesis; (iv) spleenectomy and plasmapheresis procedures which clear circulating anti-platelet antibodies; (v) increasing platelet count by platelet transfusion and bone marrow transplantation etc. All the above treatment options have potential side effects such as suppression of immunity, exposure to blood products with risk of transfusion reactions and/or transfusion transmitted diseases and hematoma.

With the short-comings of existing treatment options for autoimmune disorders such as Goodpasture's disease, Glomerulonephritis, Rheumatoid Arthritis, Systemic Lupus Erythematosus, Idiopathic Thrombocytopenia Purpura etc., it is essential for drug companies to research and develop more effective treatment with lower side effects for resolution of these chronic, life-threatening diseases.

U.S. Pat. No. 6,080,401 by Malireddy S. Reddy et al., describes use of a composition consisting mixtures of several herbs one of which being *Trigonella foenum-graecum*, along with mixtures of several probiotic preparations for treatment of wide variety of diseases namely anemia, arthritis, constipation, depression, diabetes, dyspepsia, hemorrhoids, hepatitis, hypertension, impotency, overweight, periodontal disease and combinations thereof.

U.S. Pat. No. 5,707,631 by Chaim Lieberman discloses formulation of herbal composition consisting of *Trigonella foenum-graecum, Syzygium aromatium* fruit, *Allium sativum* bulb, *Cinnamon zeylanicum* bark, *Saussurea costus* root and *Euphorbia lathyrus* bud for use in lowering cholesterol, treating arthritis, blood pressure and alzheimer's disease. However, this patent document does not disclose any evidence which can be understood and practiced by anyone skilled in the art regarding any action of this composition in arthritis in this patent.

Chopra et al. (2010) has recently published a poly-herbal composition comprising extract of *Trigonella foenum-graecum* (Fenugreek) along with extracts of *Boswellia serrata* (Salai Guggul), *Linum usitatissimum* (Flaxseed), *Camellia sinensis* (Green tea), *Curcuma longa* (Turmeric), *Tribulus terrestris* (Gokshur) and *Piper nigrum* (Black pepper) used for treatment of RA.

Khan et al. (2011) clinically evaluated a herbal composition comprising *Nigella sativa, Withania somnifera, Smilax china, Apium graveolens, Trigonella foenum graecum, Zingiber officinale* and *Colchicum autumnale* for treatment of Rheumatoid Arthritis.

All the above discussed prior art discloses composition consisting of several herbs and it is difficult to establish that the *Trigonella foenum-graecum* is contributing to the beneficial effects claimed.

*Trigonella foenum-graecum* or fenugreek is most commonly used in traditional medicine. Extracts of fenugreek seeds are investigated for treatment of various diseases like diabetes, gout, stomach ulcers, diarrhea, constipation etc. Ahmadiani et al. (2001) studied the anti-inflammatory and anti-pyretic activity of fenugreek. Vyas et al. (2008) showed that extract of fenugreek seeds have analgesic and anti-inflammatory activities. These studies do not illustrate or teach specific components or chemical composition in fenugreek seeds which contribute to the claimed activities.

Fenugreek seeds are composed of many chemical substances namely Alkaloids like Trigonelline, Gentianine, Carpaine, Choline; Amino acids like 4-Hydroxyisoleucine, Histidine, Lysine, Arginine; Flavonoids—Luteolin, Quercetin, Vitexin, Isovitexin, Orientin, Isoorientin, Vicenin-1, Vicenin-2; Furostanol Saponins—Triogenelloside C, Trigofoenosides, Trigoneosides, Fenugrin B; Spirostanol Saponins-Graecunins, Fenugreekine; Sapinogens—Diosgenin, Yamogenin, Yuccagenin, Lilagenin, Tigogenin, Neotigogenin, Gitogenin, Neogitogenin, Sarsasapogenin, Smilagenin; Anthocyanins; Fiber—Gum; Other phenolic components—Trigocoumarin, Scopoletin, Chlorogenic, Caffeic and p-Coumaric acids; Lipids; Vitamins and traces of inorganic elements.

The main embodiment of the present disclosure is a composition comprising Trigoneoside Ib and Vicenin-1 for treatment of autoimmune disorders such as Goodpasture's diseases, Glomerulonephritis and Rheumatoid Arthritis. The novelty and inventiveness of this disclosure resides in the unique composition of Trigoneoside Ib and Vicenin-1. Trigoneoside Ib has been reported as one of the many furostanol saponins present in fenugreek seeds. Structure of Trigoneoside Ib is shown in FIG. 1. Yoshikawa et al. (1997) and Murakami et al. (2000) have characterized all the Trigoneosides present in fenugreek and reported $^{13}$C NMR, $^1$H NMR and $[\alpha]_D$ data for these molecules. Trigoneoside Ia, Ib and XIb are structural isomers with molecular weight of 906 with comparable NMR data and different $[\alpha]_D$ data. Identification of specific isomer can be carried out using acid hydrolysis in which Trigoneoside Ia gives a neogitogenin, Trigoneoside Ib gives a gitogenin and Trigonesoside XIb gives an L-rhamnose.

Many flavonoid glycosides are present in fenugreek seed namely vitexin, isovitexin, orientin, isoorentin, vicenin etc. These flavonoids have been investigated for various physiological activities like anti-oxidative, anti-thyroid, anti-apoptic, anti-inflammatory, anti-nociceptive, anxiolytic etc. The present disclosure is related to one of the flavonoid glycoside Vicenin-1. Presence of Vicenin-1 in fenugreek is reported by Wagner et al. (1973). Structure of Vicenin-1 is shown in FIG. 2. Other plant species containing Vicenin-1 are *Linum usitatissimum, Tragopogon porrifolius* and *Triticum aestivum*. Sato et al. (2010) has disclosed a method of synthesis of Vicenin-1 and provided comparative data of $^{13}$C NMR for synthetic and naturally obtained Vicenin-1.

SUMMARY OF THE INVENTION

Accordingly, the present disclosure relates to a composition comprising Trigoneoside Ib and Vicenin-1 optionally along with at least one acceptable excipient; a method of preparing a composition comprising Trigoneoside Ib and Vicenin-1 optionally along with at least one excipient, said method comprising act of: a) flaking *Trigonella* seeds, b) extracting flaked *Trigonella* seeds with a solvent mixture followed by filtering and concentrating to obtain a semisolid mass, c) dissolving the mass to obtain a clear solution, d) counter current extracting the clear solution with n-butanol to obtain a solution comprising an aqueous layer and butanol layer, e) passing the aqueous layer through ion exchange resin and adsorbent column to obtain an eluant comprising the Trigoneoside Ib and the Vicenin-1, f) purifying the eluant to obtain free flowing powder and g) optionally adding at least one excipient to obtain the composition; and a method of treating autoimmune disorders said method comprising acts of administering a composition comprising Trigoneoside Ib and Vicenin-1 optionally along with at least one excipient, to a subject in need thereof.

Figure 1:
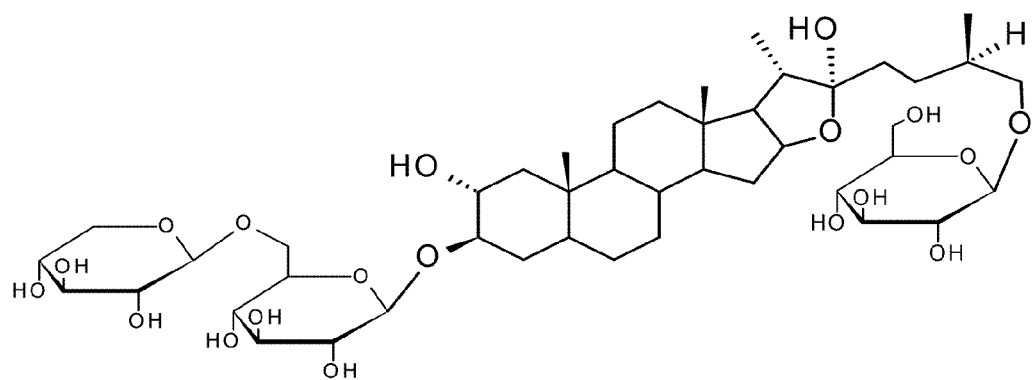
FIG. 1 shows structure of Trigoneoside Ib.
Figure 2:
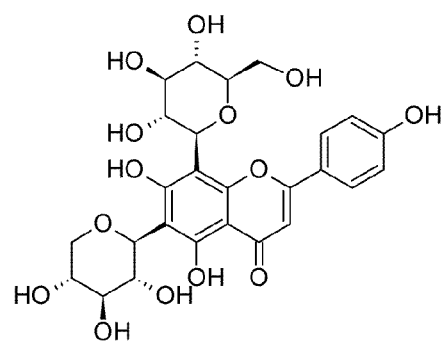
FIG. 2 shows structure of Vicenin-1.

(Left) GBM+Test Composition (75 mg/kg) group; (1) Space of urine formation, (2) Destruction of glomeruli; (3) Tubular swelling; (4) Tubular casts; (5) Cellular infiltration; (6) Glomerulitis Immunological Reaction.

DETAILED DESCRIPTION OF THE PREFERRED EMBODIMENT

The present disclosure relates to a composition comprising Trigoneoside Ib and Vicenin-1 optionally along with at least one excipient.

In an embodiment of the present disclosure, the Trigoneoside Ib ranges in concentration from about 40% (w/w) to about 90% (w/w) and Vicenin-1 ranges in concentration from about from 1% (w/w) to about 20% (w/w).

In another embodiment of the present disclosure, the Trigoneoside Ib and the Vicenin-1 are obtained from a plant *Trigonella foenum-graecum*.

In yet another embodiment of the present disclosure, the excipient is selected from a group comprising granulating agents, binding agents, lubricating agents, disintegrating agents, sweetening agents, coloring agents, flavoring agents, coating agents, plasticizers, preservatives, suspending agents, emulsifying agents, cellulosic material and spheronization agents or any combination thereof.

In still another embodiment of the present disclosure, the composition is formulated into dosage forms selected from a group comprising tablet, capsule, troches, lozenges, powder, syrup, solution, aerosol, suspension, dispersible powders or granules, emulsion in hard or soft gel capsules, syrups, elixirs, liniment, ointment, skin patch, phyotceuticals, nutraceuticals and food stuffs.

The present disclosure also relates to a method of preparing a composition comprising Trigoneoside Ib and Vicenin-1 optionally along with at least one excipient, said method comprising act of:
   a. flaking *Trigonella* seeds;
   b. extracting flaked *Trigonella* seeds with a solvent mixture followed by filtering and concentrating to obtain a semisolid mass;
   c. dissolving the mass to obtain a clear solution;
   d. counter current extracting the clear solution with n-butanol to obtain a solution comprising an aqueous layer and butanol layer;
   e. passing the aqueous layer through ion exchange resin and adsorbent column to obtain an eluant comprising the Trigoneoside Ib and the Vicenin-1;
   f. purifying the eluant to obtain free flowing powder; and
   g. optionally adding at least one excipient to obtain the composition.

In an embodiment of the present disclosure, the seeds are flaked to a size ranging from about 1 mm to about 5 mm more particularly 2 mm.

In another embodiment of the present disclosure the solvent mixture comprises an aliphatic alcohol and water in ratio of about 1:1 to about 9:1 more particularly 4:1.

In yet another embodiment of the present disclosure, the aliphatic alcohol is selected from a group comprising methyl alcohol, ethyl alcohol, propyl alcohol and iso-propyl alcohol or any combination thereof.

In still another embodiment of the present disclosure, the mass was dissolved in deionized water.

In still another embodiment of the present disclosure, the purification is carried out to obtain the Trigoneoside Ib having a purity ranging from about 90% to about 95% and the Vicenin 1 having a purity ranging from about 90% to about 95%.

In still another embodiment of the present disclosure, the purification comprises steps of buffer treatment followed by alcohol or acid treatment and concentration to obtain purified free flowing powder.

In still another embodiment of the present disclosure, the concentration is carried out at a temperature ranging from about 40° C. to about 80° C., more particularly about 50° C.

In still another embodiment of the present disclosure, the composition has the Trigoneoside Ib ranging in concentration from about 40% (w/w) to about 90% (w/w) and the Vicenin-1 ranging in concentration from about 1% (w/w) to about 20% (w/w).

In still another embodiment of the present disclosure, the excipient are selected from a group comprising granulating agents, binding agents, lubricating agents, disintegrating agents, sweetening agents, coloring agents, flavoring agents, coating agents, plasticizers, preservatives, suspending agents, emulsifying agents, cellulosic material and spheronization agents or any combination thereof.

The present disclosure also relates to a method of treating autoimmune disorders said method comprising acts of administering a composition comprising Trigoneoside Ib and Vicenin-1 optionally along with at least one excipient, to a subject in need thereof.

In an embodiment of the present disclosure, the autoimmune disorder is selected from a group comprising Goodpasture's disease, Glomerulonephritis, Rheumatoid Arthritis, Systemic Lupus Erythematosus and Idiopathic Thrombocytopenia Purpura.

In another embodiment of the present disclosure, the subject is an animal or human being.

In yet another embodiment of the present disclosure, the composition in administered in daily dosage ranging from about 1 mg/kg to about 100 mg/kg in animal and about 1 mg/kg to about 50 mg/kg in human being.

The present disclosure is also related to use of a composition comprising 40-90% (w/w) Trigoneoside Ib and 1-20% (w/w) of Vicenin-1 in treatment of Goodpasture's disease, Glomerulonephritis, Rheumatoid Arthritis, Systemic Lupus Erythematosus and Idiopathic Thrombocytopenia Purpura by preventing the autoantibody mediated damage to the organs. The method of arriving at a specific composition comprising Trigoneoside Ib and Vicenin-1 from fenugreek seeds is not known in the art. The uniqueness of the process disclosed in the present disclosure is in the extraction of a composition specifically comprising Trigoneoside Ib and Vicenin-1. Further purification is carried out to obtain 90-95% purified Trigoneoside Ib and 95% pure Vicenin-1 for structural characterization and standardization of the composition.

In another embodiment of the present disclosure, Trigoneoside Ib has molecular weight 906 and chemical formula of $C_{44}H_{74}O_{19}$.

In still another embodiment of the present disclosure, Vicenin-1 has molecular weight of 564 and a chemical formula of $C_{26}H_{28}O_{14}$.

In still another embodiment of the present disclosure, the said composition is obtained from plant *Trigonella foenum graecum*.

In another embodiment of the present disclosure, the composition is in a form selected from a group comprising tablet, capsule, troches, lozenges, powder, syrup, solution, aerosol, suspension, dispersible powders or granules, emulsion in hard or soft gel capsules, syrups, elixirs, liniment, ointment, skin patch, phyotceuticals, nutraceuticals and food stuffs.

The present disclosure is also related to a process of the extraction and purification of composition comprising Trigoneoside Ib and Vicenin-1 from *Trigonella foenum-greacum* and the process steps comprising the following:
a. Extracting clear solution by defatting and removal of nitrogenous compounds like alkaloids, amino acids; and
b. Passing clear solution through cation exchange macroporous resin and adsorbent column to elute Trigoneoside Ib and Vicenin-1; concentration of eluant and further purification.

In one embodiment of the present disclosure, the composition ranges from 40-90% (w/w) of Trigoneoside Ib and 1-20% (w/w) Vicenin-1.

Figure 3:
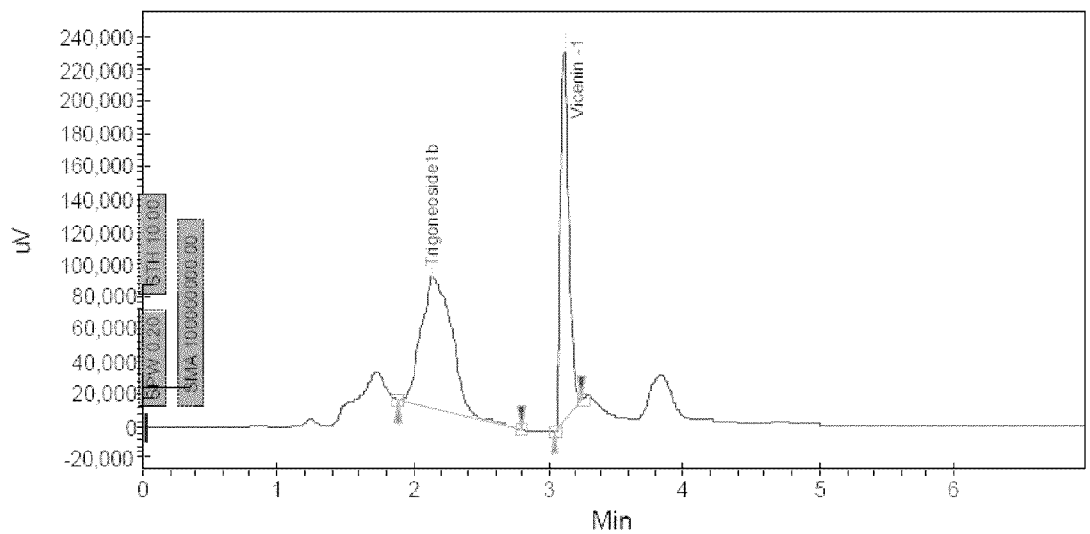
FIG. 3 shows HPLC chromatogram of 46% Trigoneoside Ib and 6% Vicenin-1.
Figure 4:
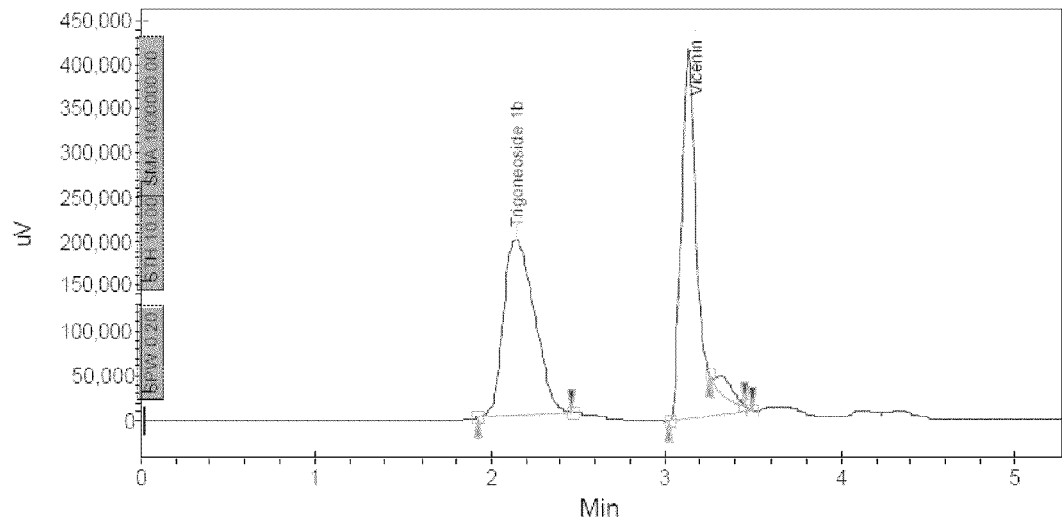
FIG. 4 shows HPLC chromatogram of 76% Trigoneoside Ib and 15% Vicenin-1.
Figure 5:
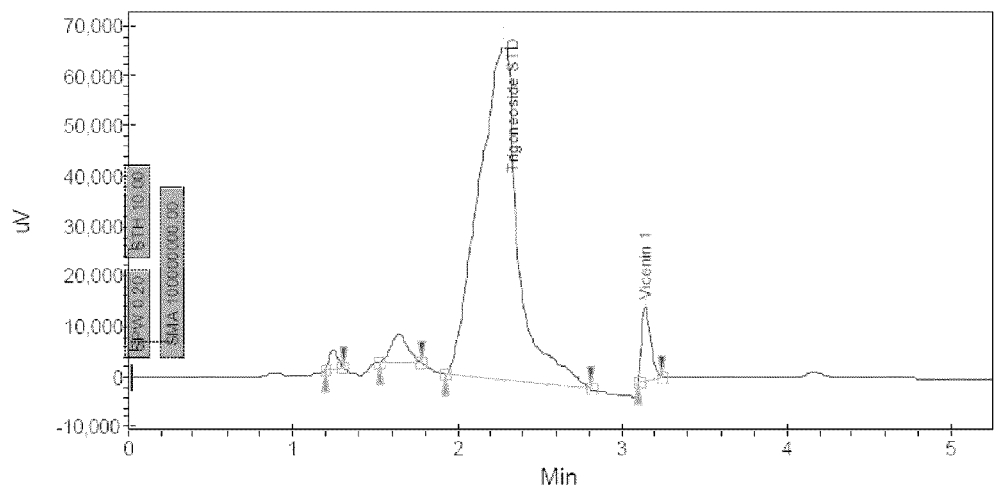
FIG. 5 shows HPLC chromatogram of 91% Trigoneoside Ib and 5% Vicenin-1.

In another embodiment of the present disclosure, since Trigoneoside Ib and Vicenin-1 are extracted from fenugreek seed, it is implied that the composition may comprise of cellulosic material containing benign molecules from fenugreek seed in small proportions as seen from the HPLC results. (FIGS. 3-5)

In another embodiment of the present disclosure, the extraction of clear solution from *Trigonella foenum-greacum* in step (a) consists of following steps:
i. flaking fenugreek seeds;
ii. extracting flaked seeds with solvent;
iii. filtering extract to get clear solution;
iv. concentrating clear solution under vacuum to obtain a semisolid mass;
v. dissolving concentrated mass to obtain a clear solution;
vi. counter current extraction of clear solution with n-butanol to remove fatty matter;

In one embodiment of the present disclosure, the solvent used in step (b) is a mixture of water and alcohol selected from a group comprising methyl alcohol, ethyl alcohol, propyl alcohol and isopropyl alcohol, in a ratio ranging from 1:1 to 9:1 and preferably 4:1.

In still another embodiment of the present disclosure, the extraction is carried out for a time period ranging from about 8 hrs to 12 hrs and preferably about 10 hrs.

In still another embodiment of the present disclosure, the extraction is carried out at a temperature ranging from about 30° C. to about 40° C. and preferably about 35° C.

In still another embodiment of the present disclosure, the extract is concentrated under vacuum at a temperature ranging from about 45° C. to about 55° C. and preferably about 50° C.

In still another embodiment of the present disclosure, the concentrated mass is dissolved in deionized water.

In another embodiment of the present disclosure, composition comprising Trigoneoside Ib and Vicenin-1 are obtained from the clear solution in step (b) using following steps:
i. Passing clear water layer through cation exchange macroporous resin and adsorbent column to elute Trigoneoside Ib and Vicenin-1;
ii. Concentration of eluant and spray drying.

In still another embodiment of the present disclosure, the adsorbent column is selected from a group comprising acid cation exchange macroporous resin, Sephadex LH-20, Dowex Optipore L493 or its equivalent.

In still another embodiment of the present disclosure, the elution of adsorbent column is carried out with water and ethyl alcohol with initial ratio of 30:70 followed by a shift to ratio of 5:95.

In still another embodiment of the present disclosure, the elution of adsorbent column is carried out for about 1 hr to about 4 hrs, preferably about 2 hrs.

In still another embodiment of the present disclosure, the concentrated mass in spray dried at about 110° C. to about 130° C., preferably about 120° C.

Yet another embodiment of the present disclosure is related to a process of purification of Trigoneoside Ib and the process steps comprising the following:
i. dissolving concentrated eluent in buffer and filtering insolubles;
ii. washing buffer solution with n-butanol;
iii. concentration of n-butanol fractions;
iv. redissolving concentrated fraction in solvent; and
v. passing resulting solution through adsorbent column.

In still another embodiment of the present disclosure, the buffer solution is selected from a group comprising potassium dihydrogen phosphate and hydrochloric acid.

In still another embodiment of the present disclosure, the solvent used for redissolution is ethyl alcohol.

Yet another embodiment of the present disclosure is related to a process of purification of Vicenin-1 from n-butanol layer comprising of other flavonoid glycosides and the process steps comprising the following:
i. concentrating under vacuum;
ii. washing concentrate with buffer solution to remove insolubles;
iii. concentration of resulting solution to half the volume and agitation;
iv. filtration to remove impure crystals; and
v. refluxing impure crystals with solvent and filtering to get 95% pure Vicenin-1.

In still another embodiment of the present disclosure, agitation of concentrated mass was carried out for 1 hr to 48 hrs, preferably 24 hrs.

In still another embodiment of the present disclosure, agitation of concentrated mass was carried out at 30° C. to 40° C., preferably 35° C.

In still another embodiment of the present disclosure, solvent used for refluxing is methanol and methylene dichloride ranging in a ratio of 1:1.

The present disclosure is also related to a method for manufacture of medicament comprising a composition of 40-90% (w/w) of Trigoneoside Ib and 1-20% (w/w) Vicenin-1 optionally along with at least one excipient and a method of administering effective amount of the said composition for treatment and management of autoimmune diseases selected from a group comprising Goodpasture's disease, Glomerulonephritis, Rheumatoid Arthritis, Systemic Lupus Erythematosus and Idiopathic Thrombocytopenia Purpura.

The present disclosure is also in relation to a method of treatment and management of autoimmune diseases selected from a group comprising Goodpasture's disease, Glomerulonephritis, Rheumatoid Arthritis, Systemic Lupus Erythematosus and Idiopathic Thrombocytopenia Purpura.

In one embodiment of the present disclosure, the subject is selected from a group comprising both animals and human beings.

The present disclosure is further elaborated with the help of following examples. However, the examples should not be construed to limit the scope of the disclosure.

Example 1

1000 g of fenugreek seeds having moisture content less than 5% were flaked in a roller flaker to a thickness of 2 mm. The flaked material was extracted in solvent mixture (8 liters) comprising of ethyl alcohol and water in the ratio of 80:20 and passed through the layer for a period of 10 hrs at 40° C. by recycling the eluent. After 10 hrs, extract was filtered through 200 mesh cloth to get a clear solution. The clear solution was concentrated to semisolid mass under vacuum at 50° C. The concentrated mass was dissolved in 5 liters of deionized water to get a clear solution. The clear aqueous solution was subjected to counter current extraction with n-butanol. The clear water layer was passed through a column containing 200 ml of strong acid cation exchange macroporous resin for 2 hrs. The clear column outflow liquid devoid of all amino acids, proteins, Trigonelline, and other amphoteric compounds was concentrated at 50° C. and spray dried at 120° C. to get free flowing powder having composition of about 40-46% (w/w) of Trigoneoside Ib and 1-6% (w/w) Vicenin-1. Variation in composition range is attributed to seasonal changes. The yield was about 60 g. HPLC analysis was carried out at following conditions: Column—250 mm length, 4.6 mm diameter Kromasil C18 RP 5 μm; Mobile Phase—Water: Acetonitrile gradient over a period of 20 min starting from 75:25 to 65:35; Flow rate—1 ml/min; Detector wavelength—210 nm UV. HPLC output as seen in FIG. 3 showed Trigoneoside Ib peak at 2.2 minutes and Vicenin-1 peak at 3.2 minutes. The composition was established by external standardization method using purified samples of Trigoneoside Ib obtained from Example 4 and Vicenin-1 from Example 5.

Example 2

1000 g of fenugreek seeds having moisture content less than 5% were flaked in a roller flaker to a thickness of 2 mm. The flaked material was extracted in solvent mixture (8 liters) comprising of isopropyl alcohol and water in the ratio of 70:30 and passed through the layer for a period of 10 hrs at 35° C. by recycling the eluent. After 10 hrs, extract was filtered through 200 mesh cloth to get a clear solution. The clear solution was concentrated to semisolid mass under vacuum at 50° C. The concentrated mass was dissolved in 5 liters of deionized water to get a clear solution. The clear aqueous solution was subjected to counter current extraction with n-butanol. The clear water layer was passed through a column containing 200 ml of strong acid cation exchange macroporous resin for 2 hrs. The clear column outflow liquid devoid of all amino acids, proteins, Trigonelline, and other amphoteric compounds was passed again through a resin bed comprising of Dowex Optipore L493 or its equivalent over a period of 2 hrs and the adsorption process monitored by thin layer chromatography system comprising of toluene:ethylacetate:methanol:water in the ratio of 6:3:6:1. The bioactive compounds as monitored by thin layer chromatographic system started eluting when the elution process was using 95% ethyl alcohol. These fractions were collected, screened and pooled together and concentrated at 50° C. to 55-65% (w/w) of Trigoneoside Ib and 8-12% (w/w) of Vicenin-1. Variation in composition range is attributed to seasonal changes. The yield was about 15 g. HPLC analysis was carried out by the method described in Example 1. The composition was established by external standardization method using purified samples of Trigoneoside Ib obtained from Example 4 and Vicenin-1 from Example 5.

Example 3

1000 g of fenugreek seeds having moisture content less than 5% were flaked in a roller flaker to a thickness of 2 mm. The flaked material was extracted in solvent mixture (8 liters) comprising of ethyl alcohol and water in the ratio of 80:20 and passed through the layer for a period of 10 hrs at 35° C. by recycling the eluent. After 10 hrs, extract was filtered through 200 mesh cloth to get a clear solution. The clear solution was concentrated to semisolid mass under vacuum at 50° C. The concentrated mass was dissolved in 5 liters of deionized water to get a clear solution. The clear aqueous solution was subjected to counter current extraction with n-butanol. The clear water layer was passed through a column containing 200 ml of strong acid cation exchange macroporous resin for 2 hrs. The clear column outflow liquid devoid of all amino acids, proteins, Trigonelline, and other amphoteric compounds was passed again through a resin bed comprising of Dowex Optipore L493 or its equivalent over a period of 2 hrs and the adsorption process monitored by thin layer chromatography system comprising of toluene:ethylacetate:methanol:water in the ratio of 6:3:6:1. The bioactive compounds as monitored by thin layer chromatographic system started eluting when the elution process was using 70:30 ethyl alcohol: water mixture. These fractions were collected, screened and pooled together and concentrated at 50° C. to 70-76% (w/w) of Trigoneoside Ib and 15-18% (w/w) of Vicenin-1. Variation in composition range is attributed to seasonal changes. The yield was about 9 g. HPLC analysis was carried out by the method described in Example 1 and the output chromatogram is shown in FIG. 4. The composition was established by external standardization method using purified samples of Trigoneoside Ib obtained from Example 4 and Vicenin-1 from Example 5.

Pure standards of Trigoneoside Ib and Vicenin-1 are not available with the reference standard suppliers. Hence for the purpose of structural elucidation and standardization of the composition Example 4 and Example 5 were carried out to isolate purified samples of Trigoneoside Ib and Vicenin-1 respectively.

Example 4

The compositions from Example 1-3 were dissolved in 50 mM Potassium dihydrogen phosphate buffer 300 ml and the insolubles filtered off. The buffer solution was washed with n-butanol thrice (75 ml×3) and all the three fractions were concentrated independently. Fractions 1, 2 and 3 showed a purity of 85%, 68% and 40% of Trigoneoside Ib respectively. The 85% pure powdered Trigoneoside Ib was about 10% of the starting weight which was redissolved in ethyl alcohol and passed through a bed of Sephadex LH-20, bed volume 125 ml and the fractions were collected and screened for pure Trigoneoside Ib. The pure Trigoneoside Ib fraction was concentrated to get about 90-95% area purity which was amicable for structural characterization. The yield was about 0.2% of the starting weight of crystalline off-white powder. HPLC analysis was carried out by the method described in Example 1 and the output chromatogram is shown in FIG. 5.

The melting point was 220° C. and LCMS analysis confirmed the mass of 906 (M+Na=929). Presence of furostanol saponin structure was confirmed by thin layer chromatography (TLC) using toluene:ethylacetate:methanol:water in the ratio of 6:3:6:1, followed by 5% anisaldehide sulphuric acid spray and heating at 110° C. for 15 min showed greenish brown single spot. $^{13}$C NMR analysis in $CD_3OD$ (100 Mhz): $δ_C$ (ppm) 44.43 (C-1), 71.6 (C-2), 85.8 (C-3), 34.9 (C-4), 44.4 (C-5), 28.4 (C-6), 30.78 (C-7), 34.1 (C-8), 51.7 (C-9), 36.9 (C-10), 22.0 (C-11), 39.6 (C-12), 41.8 (C-13), 57.8 (C-14), 32.8 (C-15), 82.4 (C-16), 65.06 (C-17), 16.9 (C-18), 12.08 (C-19), 40.8 (C-20), 16.3 (C-21), 114.0 (C-22), 38.5 (C-23), 28.9 (C-24), 34.9 (C-25), 76.0 (C-26), 17.6 (C-27); Glucose-I: 102.35 (C-1'), 75.1 (C-2'), 79.3 (C-3'), 73.7 (C-4'), 77.0 (C-5'), 70.6 (C-6'); Xylose: 104.57 (C-1"), 76.05 (C-2"), 78.08 (C-3"), 72.4 (C-4"), 67.0 (C-5"); Glucose-II: 103.0 (C-1'''), 76.5 (C-2'''), 79.7 (C-3'''), 72.1 (C-4'''), 82.43 (C-5'''), 62.8 (C-6'''); $^1$H NMR analysis in $CD_3OD$: 0.744 (19-$H_3$), 0.869 (18-$H_3$), 0.959 (27-$H_3$), 1.05 (5-H), 1.51 (21-$H_3$), 2.06

(25-H), 2.206 (20-H), 3.48, 4.05 (26-H$_2$), 3.699 (3-H), 4.14 (2-H), 4.04, 5.1 (6'-H$_2$); $[\alpha]_D^{24}$ (c=0.37, Pyridine): −41.9°.

Example 5

About 8000 ml of n-butanol layer comprising of other flavonoid glycosides from examples 1-3 was concentrated under 50° C. using vacuum evaporator to 400 ml. This solution was washed twice with 50 mM potassium dihydrogen phosphate solution followed by 500 ml of 1% aqueous hydrochloric acid solution. At this stage insolubles fall out as yellow amorphous powder. The above solution was concentrated to half the volume and agitated for 24 hrs at 30 to 35° C. to allow more crystals of other flavonoid glycosides to fall out and filtered. This impure crystals were refluxed in a mixture of Methanol and Methylene dichloride 1:1 at 15° C. for 3 hrs and filtered at 5° C. to get 95% pure Vicenin-1. The yield was about 1.8 g.

The melting point was 215° C. with decomposition and LCMS analysis confirmed the mass of 564 (M+H=565). Presence of flavonoid glycoside structure further was confirmed by thin layer chromatography (TLC) using toluene:ethylacetate:methanol:water in the ratio of 6:3:6:1, followed by 5% methanolic sulphuric acid spray and heating at 110° C. for 15 min showed yellow single spot. $^{13}$C NMR analysis in CD$_3$OD (100 Mhz): $\delta_C$ (ppm) 164.57 (C-2), 103.05 (C-3), 182.7 (C-4), 161.4 (C-5), 108.55 (C-6), 158.7 (C-7), 104.1 (C-8), 155.5 (C-9), 103.1 (C-10), 122.0 (C-1'), 129.2 (C-2'), 116.45 (C-3'), 161.6 (C-4'), 116.29 (C-5'), 129.1 (C-6'); Xylose: 74.6 (C-1''), 70.5 (C-2''), 79.3 (C-3''), 70.7 (C-4''), 68.9 (C-5''); Glucose: 71.76 (C-1'''), 70.99 (C-2'''), 79.67 (C-3'''), 70.05 (C-4'''), 82.35 (C-5'''), 61.6 (C-6'''); $^1$H NMR analysis in DMSO-d$_6$ (at 25° C.): Aromatic proton corresponding to flavone proton ring −[6.79, 6.8; 7.936, 7.949; 6.897, 6.951; 8.0, 8.031], sugar protons −6-C-xyloside between 3.09 to 4.65 and 8-C-glucoside between 3.29 to 4.77.

Example 6

In an embodiment of the present disclosure, 1 g of 76% Trigoneoside Ib and 15% Vicenin-1 was blended with 14 g of 91% Trigoneoside Ib and 5% Vicenin-1 to get a composition comprising 15 g of 90% Trigoneoside Ib and 5.7% Vicenin-1. This example demonstrates method of arriving at desired composition range comprising 40-90% (w/w) Trigoneoside Ib and 1-20% (w/w) Vicenin-1 by mixing different compositions having varied concentrations of said components. It is to be understood by a person skilled in the art that the composition obtained herein may be arrived at, by mixing the components, Trigoneoside Ib and Vicenin-1, available either by extraction from plant sources or obtained by chemical synthesis of said components. Thus, fenugreek is not the sole source to arrive at the said composition. It can be obtained by mixing the synthesized components Trigoneoside Ib and Vicenin-1.

Further, the composition may also be arrived at by mixing the components, Trigoneoside Ib and Vicenin-1, as obtained in the examples described in the instant disclosure.

The test composition comprising 40-90% (w/w) Trigoneoside Ib and 1-20% (w/w) Vicenin-1 obtained from methods specified in above Examples were further tested for physiological activity in the following examples:

Example 7

Activity in Glomerulonephritis Induced in Rats

Glomerulonephritis is a major cause of kidney failure and death in autoimmune diseases like Goodpasture's diseases. This study was conducted to examine the effect of test composition comprising 76% (w/w) Trigoneoside Ib and 15% (w/w) Vicenin-1 in rat model of anti-GBM induced crescentric glomerulonephritis.

Male wistar rats weighing 180-220 g were divided into groups with 6 animals each. Glomerulonephritis was induced as specified by Chen et al. (2004) by first a subcutaneous administration of rat IgG (5 mg) in Freund's complete adjuvant (FCA) followed by GBM (0.5 ml) administration intravenously after 5 days. Animals in the treatment group received the test composition (75 mg/kg) orally twice daily for 28 days. Animals in the GBM control group did not receive any treatment. A third group of animals without induction of glomerulonephritis and treatment was kept as normal control. Urine output was measured and analyzed before induction of glomerulonephritis and after completion of treatment. On day 28, animals were sacrificed for histopathological examination of their kidneys and lungs.

TABLE 1

EFFECT ON URINE PROTEIN EXCRETION PER DAY IN GLOMERULONEPHRITIS INDUCED RATS
(in mg/day, MEAN ± SEM)

| Treatment Period | Normal Control | GBM Control | GBM + Test Composition (75 mg/kg) |
|---|---|---|---|
| Baseline | 6.08 ± 1.34 | 8.18 ± 0.46 | 5.55 ± 0.48 |
| Day 28 | 5.48 ± 1.1 | 20.35 ± 2.66### | 7.11 ± 0.62*** | n = 5;
Data analyzed by Two-way ANOVA followed by Bonferroni Post test;
$P < 0.001$ as compared to Normal Control group for respective days;
***$P < 0.001$ as compared to GBM Control group for respective days.

Urine protein excreted per day (mg/day) by animals in the GBM control group on day 28 was increased more than three times from the baseline value. Increased excretion of urine protein is an indicator of reduced kidney function. Treatment with the test drug completely normalized the urine protein excretion, maintaining it close to the baseline value.

TABLE 2

HISTOPATHOLOGICAL EXAMINATION OF THE KIDNEYS ON DAY 28

| Parameters | Normal Control | GBM Control | GBM + Test composition (75 mg/kg) |
|---|---|---|---|
| Glomeruli Destruction | -- | +++ | + |
| Tubular Swelling | -- | +++ | + |
| Tubular Casts | -- | +++ | -- |
| Cellular Infiltration | -- | +++ | + |

Pathological Grading:
Severe (+++);
Moderate (++);
Mild (+);
Absence (--).

Figure 6:
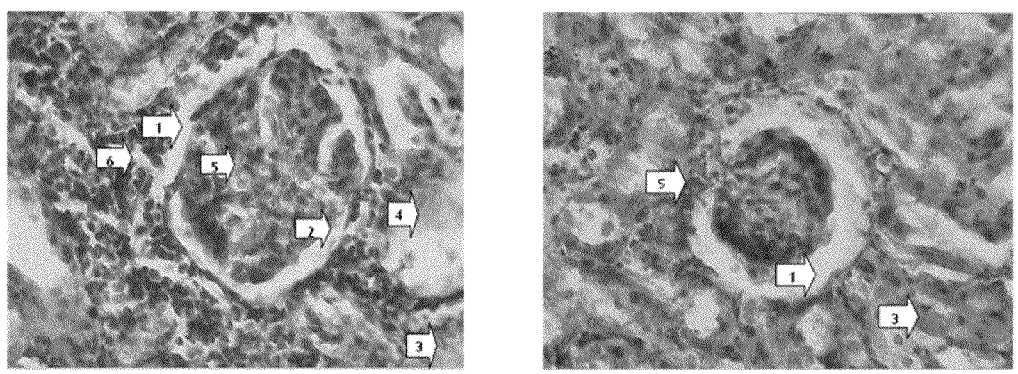
FIG. 6 shows kidney Histopathological Images of Glomerulonephritis induced Rats; (Right) GBM Control group.

Images of kidney histopathology of glomerulonephritis induced rats are shown in FIG. 6. Animals treated with test composition showed absence of tubular casts along with significantly less destruction of the glomeruli, tubular swelling and cellular infiltration, when compared to the GBM control group. Thus the pathological conditions were significantly reduced by treatment with the test composition.

TABLE 3

HISTOPATHOLOGICAL EXAMINATION OF THE LUNGS ON DAY 28

| Parameters | Normal Control | GBM Control | GBM + Test composition (75 mg/kg) |
|---|---|---|---|
| Thickening of interstitium | — | +++ | + |
| Infiltration of lymphocytes, macrophages and monocytes into interstitium | — | +++ | + |
| Extravasation of RBC into interstitium | — | +++ | — |
| Thickening of alveolar walls | — | ++ | + |
| Increase in alveolar septal chord length | — | ++ | — |

Pathological Grading:
Severe (+++);
Moderate (++);
Mild (+);
Absence (—).

Pathological effects of anti-GBM antibodies on the alveolar basement membrane in the lungs were also examined. Histopathological examination of the lungs of animals in the GBM control group showed markedly increased alveolar wall thickness, increased alveolar septal chord length along with thickened lung interstitium, severe inflammation as evidenced by infiltration of lymphocytes, macrophages and monocytes into the interstitium, and prominent extravasation of RBCs into the interstitium. Animals treated with the test composition showed significant reduction in all the above pathological conditions indicating beneficial activity of the test composition in preventing lung damage by antibodies.

The test composition effectively reduced damage to both kidneys and lungs induced by anti-GBM antibodies confirming activity in Goodpasture's disease which is characterized by patients suffering from both glomerulonephritis and pulmonary hemorrhage. Hence the test composition is useful in treatment of anti-GBM diseases like Glomerulonephritis, Goodpasture's disease etc.

Example 8

Anti-Inflammatory Activity of Test Composition

This test was conducted to evaluate the activity of test composition comprising 65% (w/w) Trigoneoside Ib and 10% (w/w) Vicenin-1, to inhibit inflammation caused by prostaglandins. Male wistar rats weighing 180-220 g were pretreated with test composition. One hour after pretreatment, sub-planter injection of 0.1 ml of 1% Carrageenan solution was given to the right hind paw. The induced paw edema was measured using plethysmometer (UGO Basile 7140). Inhibition of paw edema at the $3^{rd}$ hour shows the anti-inflammatory action.

Inhibition of paw edema was calculated as a percentage difference in the mean value of paw volume in the control group to that of the test composition treated group. Paw edema induced by carrageenan was significantly reduced by the test composition after the $2^{nd}$ and $3^{rd}$ hour.

TABLE 4

PERCENTAGE INHIBITION OF CARRAGEENAN INDUCED PAW EDEMA

| Time after Carrageenan Injection | Dose | % Inhibition of Paw Edema after 2 Hrs | % Inhibition of Paw Edema after 3 Hrs |
|---|---|---|---|
| Normal Control | — | — | — |
| Test composition | 5 mg/kg | 41.56* | 40.49*** |
|  | 10 mg/kg | 49.74** | 36.05** |
|  | 25 mg/kg | 77.76* | 63.72* | n = 6;
Data analyzed by Two-way ANOVA followed by Bonferroni post test;
***$P < 0.001$,
**$P < 0.01$ and
*$P < 0.05$ as compared to Normal Control group for respective hours.

Example 9

In-Vitro Cytokine Inhibition of Test Composition

Lipopolysaccharide (LPS) is a component of gram-negative bacteria which can induce overproduction of Nitric Oxide which in turn stimulate cytokine secretion. Human Peripheral Blood Mononuclear Cell (PBMC) system was stimulated using LPS for expression of IL-1β, IL-6 and TNF-α. The activity of the test composition in inhibiting release of these pro-inflammatory cytokines was tested. The test compositions showed significant inhibitory activity against secretion of pro-inflammatory cytokine.

TABLE 5

$EC_{50}$ VALUE OF CYTOKINE INHIBITION (μg/ml)

|  | Test composition comprising 76% Trigoneoside Ib and 15% Vicenin-1 | Test composition comprising 46% Trigoneoside Ib and 5% Vicenin-1 |
|---|---|---|
| IL-1β | 94 | 211 |
| IL-6 | 95 | 42 |
| TNF-α | 58 | 133 |

Example 10

Anti-Arthritic Action of Test Composition

Anti-arthritis activity was studied by injecting Freund's complete adjuvant (FCA) in rat paw and measuring the edema formation and percentage inhibition of paw volume in the non-injected paw.

Male wistar rats weighing between 190-250 g were injected with 0.1 ml of FCA into the sub planter region of left hind paw. 0.1 ml of FCA solution consist of 6 mg of Complete Fraction of Mycobacterium Butyrium (Difco) being Suspended in heavy Paraffin Oil (Merck). Local oedema was produced after few hrs. Treatment with the test compound was carried out from day 13 to day 21 after FCA injection. Volume of the non-injected hind paw was recorded using plethysmometer (UGO Basile 7140).

The percentage inhibition of inflammation in the non-injected paw was measured as difference in the mean paw volume of the FCA control group to that of the treated animals. Significant reduction of joint swelling induced by FCA was observed at both 5 days (Day 18) and 8 days (Day 21) after start treatment with test composition. Test composition showed nearly 80% reduction of the arthritis.

TABLE 6

PERCENTAGE REDUCTION OF FCA INDUCED ARTHRITIS

| Treatment Groups | Dose | Day 18 | Day 21 |
|---|---|---|---|
| Normal Control | — | — | — |
| Celecoxib | 10 mg/kg | 58.97 ± 35.93*** | 81.24 ± 22.35*** |
| Test composition comprising 46% Trigoneoside Ib and 5% Vicenin-1 | 50 mg/kg | 19.78 ± 45.01 | 41.63 ± 18.64 |
| | 100 mg/kg | 9.06 ± 32.89 | 78.47 ± 22.55*** |
| | 200 mg/kg | 17.93 ± 44.05 | 39.81 ± 18.76 |
| Test composition comprising 76% | 10 mg/kg | 53.86 ± 8.8*** | 49.27 ± 8.69*** |
| | 25 mg/kg | 49.36 ± 12.27*** | 57.59 ± 9.37*** |

TABLE 6-continued

PERCENTAGE REDUCTION OF FCA INDUCED ARTHRITIS

| Treatment Groups | Dose | Day 18 | Day 21 |
|---|---|---|---|
| Trigoneoside Ib and 15% Vicenin-1 | 50 mg/kg | 57.56 ± 10.12* | 80.25 ± 10.59* | n = 6;
Data analyzed by Two-way ANOVA followed by Bonferroni Post test;
P < 0.01 as compared to Normal Control group for respective days;
***P < 0.001 as compared to FCA Control group for respective days.

Example 11

Anecdotal Study of Test Composition in Rheumatoid Arthritis Patients

A prospective study was carried out in 5 Rheumatoid Arthritis (RA) patients aged between 45-60 years. The patients were administered capsules of test composition at a dose of 500 mg twice daily for a period of 1 year and the efficacy of the test composition was analyzed on the basis of patient reported outcome in a Health Assessment Questionnaire (HAQ) published by Kumar et al. (Rheumatology, Vol. 41, pp. 1457-1459, 2002).

TABLE 7

PATIENT REPORTED HEALTH ASSESSMENT QUESTIONNAIRE FOR RHEUMATOID ARTHRITIS

| Activity of Daily Living | Patient 1 | | Patient 2 | | Patient 3 | | Patient 4 | | Patient 5 | |
|---|---|---|---|---|---|---|---|---|---|---|
| | Before | After | Before | After | Before | After | Before | After | Before | After |
| Dress yourself, including tying sari/salwar/dhoti/pyjama and doing buttons? | 1 | 0 | 2 | 1 | 3 | 1 | 3 | 2 | 2 | 1 |
| Get in and out of bed? | 1 | 0 | 3 | 2 | 3 | 1 | 3 | 2 | 2 | 1 |
| Lift a full cup or glass to your mouth? | 1 | 0 | 2 | 1 | 2 | 1 | 3 | 2 | 1 | 0 |
| Walk outdoors on flat ground? | 1 | 0 | 2 | 1 | 3 | 1 | 3 | 2 | 2 | 1 |
| Wash and dry your entire body? | 1 | 0 | 2 | 1 | 2 | 1 | 3 | 2 | 2 | 1 |
| Squat in the toilet or sit cross-legged on the floor? | 2 | 1 | 3 | 2 | 3 | 2 | 3 | 3 | 3 | 2 |
| Bend down to pick up clothing from the floor? | 2 | 1 | 3 | 2 | 3 | 2 | 3 | 3 | 2 | 1 |
| Turn a tap on and off? | 1 | 0 | 2 | 1 | 2 | 1 | 3 | 2 | 2 | 1 |
| Get in and out of vehicle - autorickshaw or car? | 1 | 1 | 3 | 2 | 3 | 1 | 3 | 2 | 2 | 1 |
| Walk three kilometres? | 2 | 1 | 3 | 3 | 3 | 2 | 3 | 2 | 3 | 2 |
| Shop in a vegetable market? | 0 | 0 | 1 | 1 | 3 | 1 | 3 | 2 | 2 | 1 |

TABLE 7-continued

PATIENT REPORTED HEALTH ASSESSMENT QUESTIONNAIRE
FOR RHEUMATOID ARTHRITIS

| Activity of Daily Living | Patient 1 | | Patient 2 | | Patient 3 | | Patient 4 | | Patient 5 | |
|---|---|---|---|---|---|---|---|---|---|---|
| | Before | After | Before | After | Before | After | Before | After | Before | After |
| Climb a flight of stairs? | 2 | 1 | 3 | 2 | 3 | 2 | 3 | 3 | 2 | 2 |
| Disability score | 1.25 | 0.42 | 2.42 | 1.58 | 2.75 | 1.33 | 3.0 | 2.25 | 2.08 | 1.17 |

Scoring (0-3):
0—Without any difficulty;
1—With some difficulty;
2—With much difficulty;
3—Unable to do.
Disability score calculated as sum of all scores divided by 12.

Individual health assessment score of the anecdotal study patients before the beginning of treatment with test composition and after 1 year of treatment are given in Table 7. The disability score was calculated as sum of all scores divided by 12. All patients showed improvement in disability score. At start of the study, 4 out of 5 patients were in severe disability score range of 2 to 3. Following 12 months of treatment with the test composition, only 1 out of 5 patients remained in the severe disability score range of 2 to 3. Significant improvement in daily activities was seen and patients had greater than 90% compliance to the test composition. Hence the test composition was found to be safe and useful in treatment of patients diagnosed with Rheumatoid Arthritis.

Example 12

Formulation of Test Composition

The capsules in Example 11 were prepared by granulation of test composition comprising 76% (w/w) Trigoneoside Ib and 15% (w/w) Vicenin-1 by blending with 1.5% w/w of micro crystalline cellulose, 1% w/w of pregelatinized starch disintegrant, 0.5% w/w of crospovidone and 0.5% w/w of magnesium stearate antiadherent. The admixed granulate was filled in the capsules.

Similar formulation of the test composition ranging from 40-90% (w/w) Trigoneoside Ib and 1-20% (w/w) Vicenin-1 can be made by addition of excipient selected from a list comprising the following: granulating agents, binding agents, lubricating agents, disintegrating agents, sweetening agents, coloring agents, flavoring agents, coating agents, plasticizers, preservatives, suspending agents, emulsifying agents, spheronization agents and any combinations thereof. And the type of formulation can be selected from a group consisting of tablet, capsule, troches, lozenges, powder, syrup, solution, aerosol, suspension, dispersible powders or granules, emulsion in hard or soft gel capsules, syrups, elixirs, liniment, ointment, skin patch, phyotceuticals, nutraceuticals and food stuffs. Depending on the route of administration, different excipients/carriers may be used. Those skilled in art can choose a suitable formulation of the test composition for treatment of autoimmune diseases namely Goodpasture's disease, Glomerulonephritis, Rheumatoid Arthritis, Systemic Lupus Erythematosus and Idiopathic Thrombocytopenia Purpura.

Example 13

Anecdotal Study in Systemic Lupus Erythematosus (SLE) Patients

A prospective study was carried out in 3 patients diagnosed with Systemic Lupus Erythematosus (SLE) aged between 35-50 years for a period of 6 months. Test composition formulation as described in example 12 was administered at a dose of two 500 mg capsules twice daily. The activity of the test composition was monitored by tracking laboratory parameters and daily activity index.

Treatment with test composition significantly improved kidney function, blood parameters along with reduction in joint pain, alopecia, skin rashes and mouth ulcers. These results were supported by improvement in the SLE Daily Activity Index (SLEDAI) scores from 20 at the start of the treatment to 10 at the end of treatment for patient 1. Similarly improvement was seen for patient 2 from 10 to 6 and patient 3 from 12 to 8 following 6 months of treatment. Hence the test composition was found to be useful in treatment and management of SLE.

Example 14

Activity of Test Composition against Idiopathic Thrombocytopenia Purpura (ITP)

Balb-c mice were checked for baseline platelet count to be within physiological limits and divided into 3 groups. Idiopathic Thrombocytopenia Purpura (ITP) was induced by intraperitoneal injection of 4 μg of rat anti-mouse integrin $α_{IIb}$ antibodies to animals in the ITP control group and test composition treatment group. Animals in the treatment group received 75 mg/kg of test composition comprising 76% (w/w) Trigoneoside Ib and 15% (w/w) Vicenin-1 one hour before induction of ITP. Animals in the normal control group were neither induced with ITP nor received any treatment. Three hours after of induction of ITP, blood was withdrawn from animals in all groups to analyze platelet count.

TABLE 8

EFFECT OF TEST COMPOSITION ON PLATELET COUNT

| Treatment Group | Percentage Reduction in Platelet Count |
|---|---|
| Normal Control | 22% |
| ITP Control | 60% |
| Test Composition (75 mg/kg) + ITP | 16.5% |

Animals treated with the test composition showed significantly lower platelet reduction of 16.5% only as compared 60% in the ITP control animals following administration of anti-platelet antibodies. Normal control animals also showed platelet reduction of 22%. This reduction was attributed to the subsequent withdrawal of blood for analyzing platelet count.

The above example demonstrates that the test composition is effective against antibodies mediated reduction of platelet count and hence useful in treatment and management of ITP and/or thrombocytopenia.

What is claimed is:

1. A composition consisting of Trigoneoside Ib and Vicenin-1, optionally along with at least one excipient.

2. The composition as claimed in claim 1, wherein the Trigoneoside Ib ranges in concentration from about 40% (w/w) to about 90% (w/w) and Vicenin-1 ranges in concentration from about from 1% (w/w) to about 20% (w/w).

3. The composition as claimed in claim 1, wherein the Trigoneoside Ib and the Vicenin-1 are obtained from a plant *Trigonella foenum-graecum*.

4. The composition as claimed in claim 1, wherein the excipient is selected from the group consisting of granulating agents, binding agents, lubricating agents, disintegrating agents, sweetening agents, coloring agents, flavoring agents, coating agents, plasticizers, preservatives, suspending agents, emulsifying agents, cellulosic material and spheronization agents or any combination thereof.

5. The composition as claimed in claim 1, wherein the composition is formulated into dosage forms selected from the group consisting of tablet, capsule, troches, lozenges, powder, syrup, solution, aerosol, suspension, dispersible powders or granules, emulsion in hard or soft gel capsules, syrups, elixirs, liniment, ointment, skin patch, phyotceuticals, nutraceuticals and food stuffs.

6. A method of preparing a composition according to claim 1, said method comprising:
   a. flaking *Trigonella* seeds;
   b. extracting flaked *Trigonella* seeds with a solvent mixture followed by filtering and concentrating to obtain a semi-solid mass;
   c. dissolving the mass to obtain a clear solution;
   d. counter current extracting the clear solution with n-butanol to obtain a solution comprising an aqueous layer and butanol layer;
   e. passing the aqueous layer through ion exchange resin and adsorbent column to obtain an eluant comprising the Trigoneoside Ib and the Vicenin-1;
   f. purifying the eluant to obtain free flowing powder; and
   g. optionally adding at least one excipient to obtain the composition.

7. The method as claimed in claim 6, wherein the seeds are flaked to a size ranging from about 1 mm to about 5 mm.

8. The method as claimed in claim 6, wherein the solvent mixture comprises an aliphatic alcohol and water in ratio of about 1:1 to about 9:1.

9. The method as claimed in claim 8, wherein the aliphatic alcohol is selected from the group consisting of methyl alcohol, ethyl alcohol, propyl alcohol and iso-propyl alcohol or any combination thereof.

10. The method as claimed in claim 6, wherein the mass was dissolved in deionized water.

11. The method as claimed in claim 6, wherein the purification is carried out to obtain the Trigoneoside Ib having a purity ranging from about 90% to about 95% and the Vicenin 1 having a purity ranging from about 90% to about 95%.

12. The method as claimed in claim 6, wherein the purification comprises steps of buffer treatment followed by alcohol or acid treatment and concentration to obtain purified free flowing powder.

13. The method as claimed in claim 6, wherein the concentration is carried out at a temperature ranging from about 40° C. to about 80° C.

14. The method as claimed in claim 6, wherein the composition has the Trigoneoside Ib ranging in concentration from about 40% (w/w) to about 90% (w/w) and the Vicenin-1 ranging in concentration from about 1% (w/w) to about 20% (w/w).

15. The method as claimed in claim 6, wherein the excipient is selected from the group consisting of granulating agents, binding agents, lubricating agents, disintegrating agents, sweetening agents, coloring agents, flavoring agents, coating agents, plasticizers, preservatives, suspending agents, emulsifying agents, cellulosic material and spheronization agents or any combination thereof.

16. A method of treating autoimmune disorders said method comprising administering a composition according to claim 1 to a subject in need thereof.

17. The method as claimed in claim 16, wherein the autoimmune disorder is selected from the group consisting of Goodpasture's disease, Glomerulonephritis, Rheumatoid Arthritis, Systemic Lupus Erythematosus and Idiopathic Thrombocytopenia Purpura.

18. The method as claimed in claim 16, wherein the subject is an animal or human being.

19. The method as claimed in claim 16, wherein the composition in administered in daily dosage ranging from about 1 mg/kg to about 100 mg/kg in animal and about 1 mg/kg to about 50 mg/kg in human being.

20. The method of claim 6, wherein the seeds are flaked to a size of about 2 mm.

21. The method as claimed in claim 6, wherein the solvent mixture comprises an aliphatic alcohol and water in ratio of about 4.1.

22. The method as claimed in claim 6, wherein the concentration is carried out at a temperature of about 50° C.

* * * * *